(12) United States Patent
Comparat et al.

(10) Patent No.: US 10,405,528 B2
(45) Date of Patent: Sep. 10, 2019

(54) FARM FOR REARING INSECTS

(71) Applicant: YNSECT, Evry (FR)

(72) Inventors: Solène Comparat, Evry (FR); Antoine Hubert, Alfortville (FR); Fabrice Berro, Paris (FR); Jean-Gabriel Levon, Paris (FR); Frank Launay, Hericy (FR); Thibault Sarton Du Jonchay, Chevrières (FR)

(73) Assignee: YNSECT, Evry (FR)

( * ) Notice: Subject to any disclaimer, the term of this patent is extended or adjusted under 35 U.S.C. 154(b) by 20 days.

(21) Appl. No.: 15/565,727

(22) PCT Filed: Apr. 13, 2016

(86) PCT No.: PCT/FR2016/050849
§ 371 (c)(1),
(2) Date: Oct. 11, 2017

(87) PCT Pub. No.: WO2016/166471
PCT Pub. Date: Oct. 20, 2016

(65) Prior Publication Data
US 2018/0070566 A1 Mar. 15, 2018

(30) Foreign Application Priority Data
Apr. 13, 2015 (FR) ..................... 15 53207

(51) Int. Cl.
*A01K 67/033* (2006.01)
*B65G 1/04* (2006.01)
*B65G 1/137* (2006.01)

(52) U.S. Cl.
CPC .......... *A01K 67/033* (2013.01); *B65G 1/0407* (2013.01); *B65G 1/0414* (2013.01); *B65G 1/137* (2013.01)

(58) Field of Classification Search
CPC ............ A01K 67/033; A01K 2227/706; A01K 29/00; A01K 5/00; A01K 97/04
(Continued)

(56) References Cited

U.S. PATENT DOCUMENTS 2,670,562 A * 3/1954 Gould .................... A01K 97/04
119/6.5
3,750,625 A * 8/1973 Edwards .............. A01K 67/033
119/322

(Continued)

FOREIGN PATENT DOCUMENTS

WO WO 2014/171829 10/2014

OTHER PUBLICATIONS

International Search Report dated Sep. 15, 2016, in corresponding PCT Application No. PCT/FR2016/050849.

*Primary Examiner* — Yvonne R Abbott-Lewis
(74) *Attorney, Agent, or Firm* — Buchanan Ingersoll & Rooney PC

(57) ABSTRACT

The invention relates to a farm for rearing insects, comprising a first zone (Z1) in which the insects being reared are stored in containers while they grow and a second zone (Z2) comprising at least one station configured for effecting a rearing-related task on the insects in a container or on said container. The containers are grouped in the first zone (Z1) in sets of palletized containers referred to as basic units. The first zone (Z1) comprises pallet racks in which the basic units are disposed. The first zone (Z1) is furthermore equipped with an automated device configured to move the basic units between the first zone (Z1) and an interface (1) with the second zone (Z2).

24 Claims, 4 Drawing Sheets

(58) Field of Classification Search
USPC .................. 119/635, 300, 322, 651, 6.6, 6.7
See application file for complete search history.

(56) References Cited

U.S. PATENT DOCUMENTS

| | | | | |
|---|---|---|---|---|
| 5,351,643 | A * | 10/1994 | Hughes | A01K 67/033 |
| | | | | 119/6.5 |
| 5,433,156 | A * | 7/1995 | Hutchison | B65D 19/0012 |
| | | | | 108/51.3 |
| 5,819,685 | A | 10/1998 | Kappelt et al. | |
| 6,474,259 | B1 * | 11/2002 | Gaugler | A01K 67/033 |
| | | | | 119/6.7 |
| 6,612,247 | B1 * | 9/2003 | Pistner | B65D 19/0012 |
| | | | | 108/51.3 |
| 8,397,649 | B2 * | 3/2013 | Smith | B29C 70/865 |
| | | | | 108/57.25 |
| 9,629,339 | B2 * | 4/2017 | Newton | A01K 67/033 |
| 10,159,229 | B2 * | 12/2018 | Marchant | A01K 67/033 |
| 2011/0139075 | A1 * | 6/2011 | Shapiro Ilan | A01K 67/033 |
| | | | | 119/6.5 |
| 2011/0238207 | A1 | 9/2011 | Bastian et al. | |
| 2018/0092339 | A1 * | 4/2018 | Massaro | G06Q 50/02 |

* cited by examiner

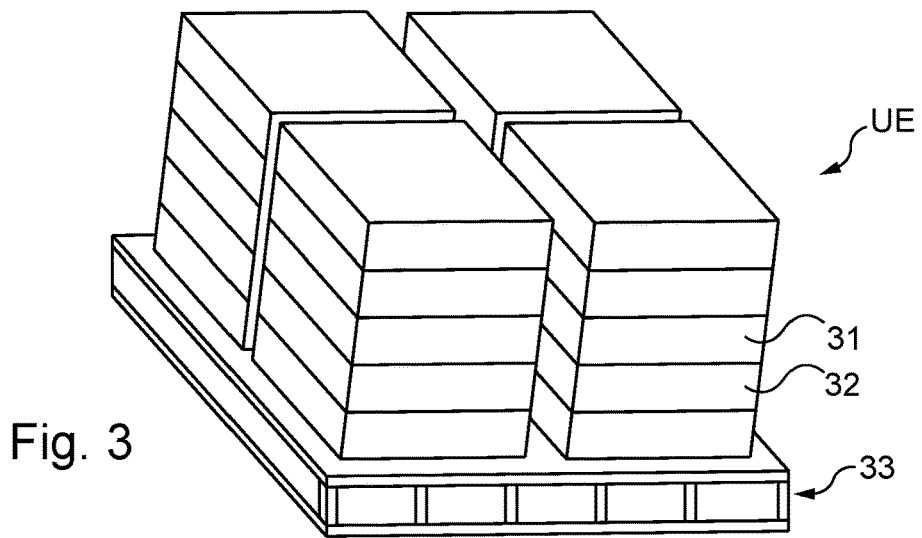
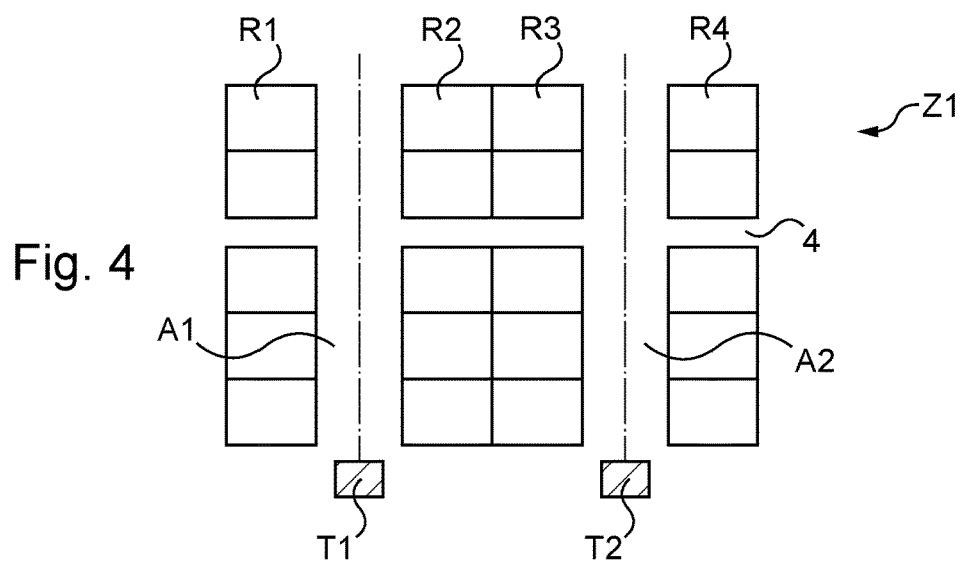
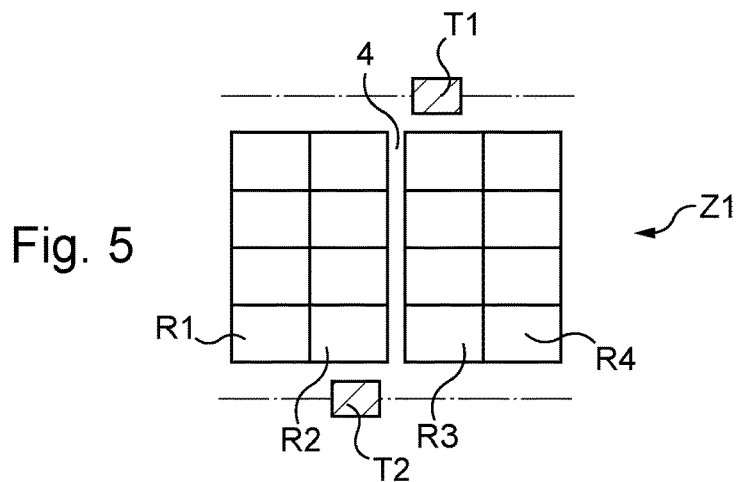

FARM FOR REARING INSECTS

CROSS-REFERENCE TO RELATED APPLICATIONS

This application is a U.S. National Stage Application pursuant to 35 U.S.C. § 371 of International Patent Application PCT/FR2016/050849, filed on Apr. 13, 2016, and published as WO 2016/166471 on Oct. 20, 2016, which claims priority to French Patent Application 1553207, filed on Apr. 13, 2015, all of which are incorporated herein by reference in their entireties for all purposes.

The present invention relates to the field of rearing insects. In particular, it relates to a farm or unit for rearing insects.

Insects, in particular certain species, can constitute a source of products or of raw materials, in particular for animal or human foodstuffs, or for use by many other industries.

Unless otherwise stated, by the term "insect" used in the present document is meant any stage of development from the egg or egg sac to the adult insect, passing through the larva and the nymph or pupa.

In particular, by the term "larva" is meant in the present document the larval stage of the insects, which includes the maggot stage for Diptera and the caterpillar stage for Lepidoptera, as well as the wingless stages in Orthoptera. By the term "nymph" is meant in the present document the intermediate stages between the larva and the imago, which includes the pupa for Diptera, the nymph for Coleoptera, the chrysalis for Lepidoptera and, if applicable, an intermediate stage during which certain physiological (prepupa) or behavioural modifications of the individuals appear, such as a significant sclerification of the cuticle for Diptera. Similarly, the term "egg" also covers an egg sac of Dictyoptera.

Typically, certain species of edible insects are rich in proteins. Approximately two thousand species of edible insects have been identified to date, and this number is increasing regularly. Many insects can be used for fodder for rearing farm animals (mammals, birds, etc.), farmed fish and aquatic invertebrates, etc. In general, insects convert a large proportion of what they ingest into body mass (in particular markedly more than mammals do). In fact, their metabolism is that of poikilothermic organisms, which do not need to use energy in order to maintain their body temperature. On the other hand, the higher animals, called homeotherms, use significant energy in order to maintain their body temperature. The domestication of insects for the purposes of feed production thus constitutes an opportunity with regard to the worldwide challenges in respect of nutrition and protection of the environment.

Apart from the food aspect, insects can constitute a significant resource in many industrial fields. Typically, the exoskeleton of insects is constituted in large part by chitin, a known derivative of which is chitosan. The applications of chitin and/or chitosan are many: cosmetics (cosmetic composition), medical and pharmaceutical (pharmaceutical composition, treatment of burns, biomaterials, corneal dressings, surgical sutures), dietetic and dietary, technical (filtering, texturing agent, flocculating agent or adsorbant, in particular for water filtration or pollution control), etc. In fact, chitin and chitosan are biocompatible, biodegradable and non-toxic materials.

Insect rearing has experienced some rapid growth. Certain processes and devices relating to such rearing have thus been developed. A process and an associated device are known for example from document WO2014/171829 making it possible to automate the supply of food in insect rearing crates. More specifically, this document discloses a device making it possible to determine, by a process of observation of each of the crates of a farm, the condition and stage of growth of the insects present in each of the crates, and if a supply of food is required in the crate in question.

Thus, although certain known devices solve certain problems of simplification in the rearing of insects, no known device and process makes it possible to envisage rearing insects on a large scale under optimized conditions.

In particular, problems of logistics and management of large-scale rearing are poorly understood and unsolved in the state of the art. Now, large-scale rearing would make it possible to obtain sufficient quantities of products in order to interest the food commodities and chemical markets in particular.

The purpose of the present invention is to overcome at least one of the aforementioned drawbacks. The present invention relates in particular to proposing a device, in particular a farm, optimizing the logistics associated with rearing insects.

In particular, the invention relates to a farm for rearing insects, comprising a first zone in which the insects being reared are stored in containers while they grow and a second zone comprising at least one station configured for carrying out a rearing operation on the insects in a container or on said container; the containers being grouped in the first zone in sets of palletized containers called basic units, the first zone comprising pallet racks in which the basic units can be arranged; the first zone also being equipped with an automated device configured for the movement of the basic units between the first zone and an interface with the second zone.

Dividing the farm into two zones makes it possible to optimize many aspects of the rearing. The first zone utilizes an automated device for collecting pallets and sending them to the second zone, in such a way that no or almost no rearing operations are conducted in the first zone. Organizing the rearing in pallets makes it possible to group together and handle a large number of single batches of insects, each batch being constituted by insects at the same stage of development or growth. Moreover, it allows for a high degree of automation, with the pallets and rearing containers being easily operated by robots or automatons. This allows high levels of production in the farm. Suitable racks can be utilized for storage of the rearing containers on pallets, allowing for significant optimization of space in the storage zone in the three spatial dimensions. The formation of basic rearing units, preferentially comprising insects at the same stage of development, allows simple sequential management of the rearing process implemented in the farm. Thus, the farm proposed in the invention makes it possible to adopt processes and production management of the industrial type that have been unknown in the field of rearing insects until now.

In such a farm for rearing insects, the automated device can advantageously comprise a storage/retrieval machine able to move along or between the racks.

The automated device can be suitable for moving inside the racks.

The automated device can for example comprise a storage/retrieval machine which moves along the racks in order to retrieve the loads at a depth of one or two racks. It can comprise a shuttle system which moves horizontally (depthwise, and if necessary, lengthwise and/or widthwise) inside the racks in order to place and collect pallets when several racks are placed side by side depthwise. The pallet recovered can for example be transferred to a storage/retrieval machine or a lift.

The containers can in particular be stackable crates, with basic units comprising a plurality of crates stacked in one or more columns on a pallet. According to another variant, the basic units comprise a rack (or shelving system) suitable for receiving the containers so as to form one or more columns of containers.

In this case, a basic unit can in particular comprise one to four columns, each constituted by four to twenty-fives crates. A basic unit can alternatively comprise one to four columns each constituted by four to thirty-five crates.

The basic units can have a height comprised between 1.80 m and 3 m, and preferably between 2 m and 2.80 m. For example, the basic units can have a height comprised between 1.80 m and 2.40 m and preferably between 2 m and 2.20 m.

Moreover, the racks can be configured for the storage of from two to fifteen basic units heightwise, and one or two basic units depthwise.

The racks can be configured for the storage of from two to twenty basic units heightwise, and one to twenty-two basic units depthwise.

According to an embodiment, the first zone can be divided into silos, intended for the storage of larvae or insects at different stages of growth and/or of different species, said silos being separated by partitioning means.

Advantageously, the farm can comprise a device for monitoring at least one environmental parameter from among the temperature, the hygrometry of the air, the atmospheric pressure, the light and the frequency thereof, the oxygen content of the air, the volatile organic compound content of the air and the fine particulate matter content of the air, configured to apply a different environmental parameter value to each set of racks.

According to an embodiment, the second zone can comprise an automated conveyor system for the movement of basic units or of degrouped containers to the at least one station of said second zone.

The second zone can in particular comprise a station for depalletizing and degrouping the containers.

The second zone can comprise a station for grouping together the containers into a basic unit.

The second zone can comprise a plurality of stations, each station being configured for one or more rearing operations selected from:
  feeding;
  providing water;
  grading the insects by size, weight, volume or density;
  sorting live and dead larvae and droppings;
  sorting live adults and dead adults;
  sorting live nymphs and dead nymphs;
  sorting at least two stages of development of the insects between eggs, larvae, nymphs and adults,
  separating live insects and the substrate that has not been consumed;
  sorting insects and eggs;
  adding insects to a rearing container;
  killing or destroying the insects;
  identifying insects having symptoms of disease;
  washing the containers.

Such a farm can comprise a station comprising a viewing and/or sampling tool configured in order to analyze the physiological state of the insects, larvae, nymphs.

Such a farm can in particular comprise a station configured for grading the adult insects by size, weight, volume or density and/or sorting live and dead larvae and droppings and/or sorting adult insects and larvae or nymphs, comprising a device for separation according to density and air intake.

The farm can comprise a station configured for grading the live larvae by size or by volume and/or sorting live and dead larvae, live and dead adult insects, live and dead nymphs, eggs, substrate and droppings, comprising an optical sorting device. Optical sorting can in particular make it possible to sort the insects by size, or according to other visually identifiable parameters such as colour, shape, movement etc.

The farm can comprise a station configured for grading live larvae and/or sorting live and dead larvae, live and dead adult insects, live and dead nymphs, eggs, substrate and droppings, comprising a vibrating element such as a screen or a vibrating table.

The farm can comprise a station configured for grading live larvae and/or sorting live and dead larvae, live and dead adult insects, live and dead nymphs, eggs, substrate and droppings, comprising a densimetric table.

The farm can comprise a station configured for grading live larvae and/or sorting live and dead larvae, live and dead adult insects, live and dead nymphs, eggs, substrate and droppings, comprising a roller grader.

The farm can comprise a station configured for grading live larvae and/or sorting live and dead larvae, live and dead adult insects, live and dead nymphs, eggs, substrate and droppings, comprising a rotating element allowing larvae to be ejected by centrifugal force.

The different stations can be supplied by automated devices. Depending on the station in question, it can be an automated supply of substrate, food, water, containers (full or empty), the contents of emptied containers etc.

The farm can comprise a device for identifying crates or basic units suitable for being implemented by electronic means.

The farm can also comprise a set of sensors comprising:
  a weight sensor configured in order to determine the weight of a basic unit or of a container; and/or
  a colour sensor, configured in order to determine the colour of the insects, nymphs or eggs, substrate, water and/or droppings in a container; and/or
  a thickness or volume sensor configured in order to determine the thickness or the volume of substrate in a container;
  a size sensor, configured in order to determine the size of the insects, nymphs or eggs in a container.

Other features and advantages of the invention will become more apparent from the following description.

In the attached drawings, given non-limitatively by way of example:
  FIG. 1 shows the overall organization of a farm according to an embodiment of the invention;
  FIG. 2 shows, in a diagrammatic three-dimensional view, an example of a farm according to an embodiment of the invention;
  FIG. 3 shows, in a diagrammatic view, a basic unit for insect rearing;
  FIG. 4 shows an example of the organization of a first zone of a farm according to an embodiment of the invention;
  FIG. 5 shows an example of the organization of a first zone of a farm according to another embodiment of the invention;
  FIG. 6 shows, in a diagrammatic three-dimensional view, a first zone of a farm according to an embodiment of the invention adopting the organization shown in FIG. 4.

Figure 1:
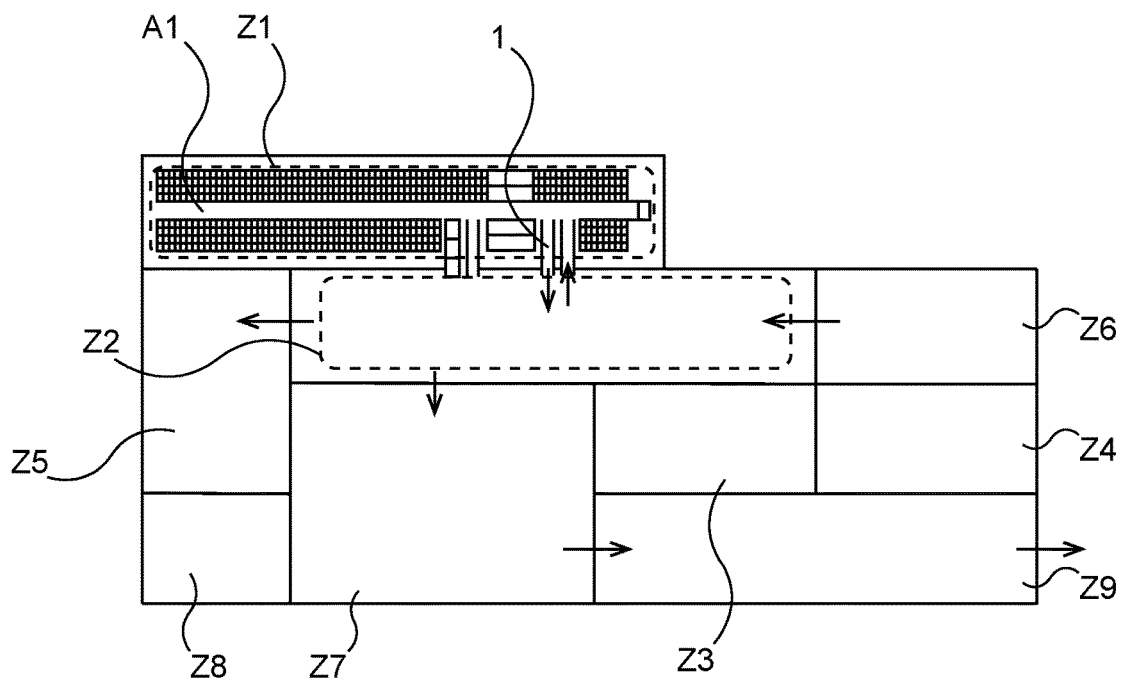

As shown in FIG. 1, a farm for rearing insects according to the invention, shown here in a diagrammatic view from above, comprises at least two zones, namely a first zone Z1 organized for the storage of insects during their growth. In this first zone Z1, the insects increase in size under controlled and optimized environmental conditions (defined by environmental parameters including temperature, hygrometry, etc.).

The concept of insect rearing comprises the growth of adult insects up to a desired stage, but can also comprise all the phases that precede obtaining an adult insect, from the laying of eggs, the development of the egg, hatching, the larval stage, nymphosis, the nymph stage, emergence etc. Insect rearing can in particular be envisaged as an organized whole allowing the laying of eggs by adult insects for the production of larvae, some larvae being reared to the adult stage for laying new eggs, the adults being regularly renewed (for example following their death) by young adults providing new egg laying and so on. The final product of the production can be eggs, and/or larvae, and/or nymphs, and/or adult insects.

The farm also comprises a second zone Z2, organized for carrying out of one or more rearing operations. The rearing operations correspond to operations that must be conducted in order to maintain life, good growth and/or the optimization of the insect rearing conditions. Among other operations, it can be:
- feeding the insects;
- providing them with water;
- renewing the substrate in which they are reared;
- sorting them (to make it possible to remove the eggs, separate the insects by size, remove those that have died during rearing etc.);
- identifying insects having symptoms of disease;
- increasing or reducing the density of the basic units in order to maximize production without prejudicing the welfare and health of the insects, in order to optimize the productivity of the farm;
- killing surplus, diseased and/or contaminated or parasitized insects;
- adding new strains of insects (so as to maintain the good health of the offspring);
- processing the droppings in order to reuse them.

The rearing substrate, i.e. the medium added to the containers suitable for the life of the insects or larvae or nymphs which can contain food intended for the insects or larvae or nymphs, can have the form of a dry solid (particles, flakes etc.), a damp solid or a liquid.

The second zone Z2 comprises in particular one or more specialized work stations for carrying out one or more rearing sequences. A rearing sequence can correspond to an operation or to a series of several operations which constitutes it. The second zone Z2 can be adapted in order to allow the implementation, at one or more work stations, of rearing sequences constituted by a succession of operations. The work stations can typically be grouped together in islands for the implementation of successive operations.

FIG. 1 shows a view for the possible organization of the first zone Z1. The insects (eggs, larvae, nymphs, or adults) are reared in containers grouped together into basic rearing units, in the form of pallets. The palettes are stored in the first zone Z1 in pallet racks. In the example shown here, the pallet racks are separated by an aisle A1 allowing movement between the racks. Several parallel sets of racks/aisles/racks can be described to constitute the zone Z1. The racks can for example comprise from 1 to 20 spaces for pallets. For example, the aisle A1 can allow an automated device, typically a storage/retrieval machine to move around, making it possible to move the basic units to an interface 1 with the second zone Z2. The interface 1 can be a zone for depositing a basic unit, for example provided with a conveyor system such as a belt conveyor, the operation of which makes it possible to send the basic unit to the second zone 2 in order to carry out a rearing operation.

Figure 2:
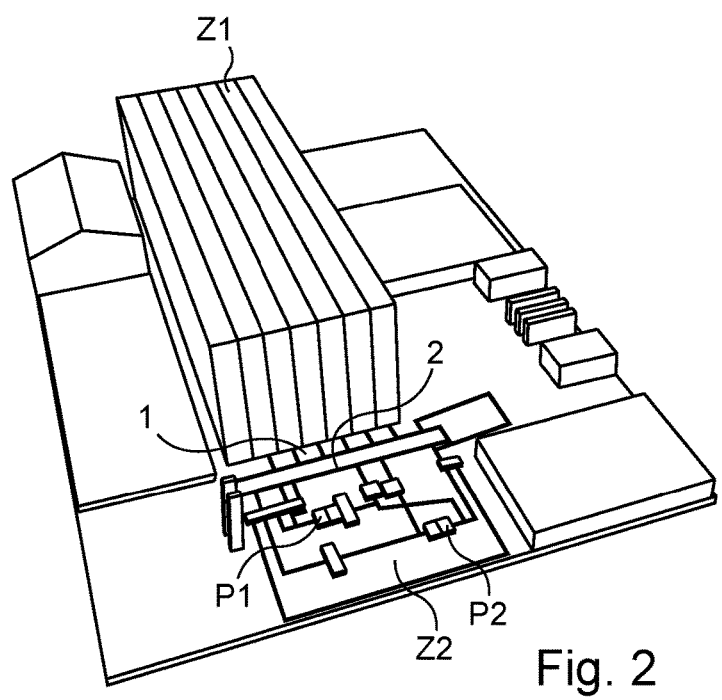

FIG. 2 shows, in a diagrammatic three-dimensional view, an example of a farm according to an embodiment of the invention. In the example shown here, the pallet racks are formed of a column and beam structure in which passages are arranged in order for storage/retrieval machines to move between the racks. The second zone Z2 comprises a belt conveyor 2 making it possible for basic units or containers which have been degrouped to be moved in said second zone Z2. The belt conveyor 2 generally allows movement in the second zone Z2 from the interface with the first zone Z1 to the one or more stations P1 and/or P2, optionally grouped in islands of stations and dedicated to one or more rearing operations, and between the stations. The belt conveyor 2 can allow the basic unit or containers to return to the interface I, or, optionally, to a second interface (not shown) dedicated to the transition of the basic units from the second zone Z2 to the first zone Z1.

In order to carry out certain operations, it can prove necessary to depalletize and/or degroup the rearing containers. According to various possible modes of organization, this operation can be carried out at the level of the interface I, or on a dedicated station of the second zone Z2.

In addition to the first zone Z1 and the second zone Z2, a farm for rearing insects according to an embodiment of the invention can comprise various additional zones: a zone for preparing rearing products Z8, in particular fluids, including those making it possible to control the atmospheric conditions of the farm, an arrival zone for new strains, a zone for dispatching strains.

The farm can have other additional zones: a laboratory zone Z3, an office zone Z4, a zone for waste treatment Z5, a zone for preparing the rearing food Z6, a zone for producing products Z7, for producing various products from the insects reared, a logistics zone Z9, etc.

In the invention, the growth of the insects i.e. the rearing phases outside of the specific rearing operations is performed in the basic rearing units. This is a set of grouped rearing containers. FIG. 3 shows an example of a rearing unit, according to a three-dimensional schematic diagram. In particular, the rearing containers can be stackable crates or compartments. By stackable crates or compartments is meant in particular crates or compartments that are superimposed on one another in a slightly embedded manner, which achieves a certain stability for the column of crates thus formed.

The stackable crates are made from a rot-proof material. They can in particular be made from plastic material. Preferably, the material used is of the food-grade type, i.e. a material permitted for contact with foodstuffs.

They can in particular be crates of simple geometry, with one or more of the following characteristics: a parallelepipedal rectangle general shape, a flat base, vertical sides (side walls). They can comprise an open upper face, in particular for rearing Coleoptera, or a closed upper face so as to form a rearing cage, in particular for rearing Diptera (typically with walls of wire mesh allowing air and light to pass through). They can also be equipped with corresponding embedding means between the upper face and the lower face, such as pins intended to be accommodated in corresponding holes when the crates are stacked.

Moreover, the crates must have sufficient vertical strength to support their stacking and be sufficiently robust in order to stand up to all of the handling, cleaning, and to the cleaning products so as to allow the reuse thereof. The number of crates stacked can vary according to different embodiments of the invention, and can for example be up to twenty crates per column of crates. Each crate can for example have a load capacity (i.e. a weight able to be stored in the crate) comprised between 0.2 and 10 kg, preferentially between 0.5 and 5 kg and more preferentially between 1 and 3 kg. Typically, the load of a crate can be of the order of 2 kg, this value being given by way of example for gregarious holometabolous larvae such as the mealworm or the soldier fly, close to the nymphosis stage. When empty, a crate can have a weight of the order of 1.5 kg. The weight of a loaded crate can thus typically be of the order of 3.5 kg.

Typically, a full column of containers can have a total weight of the order of 500 kg.

The crates advantageously have sufficient stability and strength in order to resist, even when stacked, the horizontal accelerations caused by the automated device allowing their movement in the first zone Z1 of the farm or between the first zone Z1 and the second zone Z2, and on any optional means such as a belt conveyor in the second zone Z2. In particular, the crates advantageously have sufficient horizontal strength to support an acceleration differential between their lower face and their upper face. The crates should preferably be configured to be able to resist a horizontal acceleration comprised between 1 m/s$^2$ and 5 m/s$^2$ and preferentially between 3 m/s$^2$ and 4 m/s$^2$.

The crates also advantageously have openwork side walls allowing aeration suitable for insect rearing.

As shown in FIG. 3, the containers 31, 32 are palletized, i.e. grouped together into basic units BU on a loading pallet 33. The pallet 33 can in particular be a pallet of a standard size, i.e. typically a pallet of the "Europe pallet" type, 120 cm long by 80 cm wide or a half-pallet of this type, 80 cm long by 60 cm wide. Pallets of other formats can be used, however, using a pallet of the standard format makes it possible to limit the costs associated with the specialization of equipment. A pallet made from food-grade plastic can advantageously be used. A metal pallet, for example of aluminium or aluminium alloy, can also be used. A plastic or metal pallet avoids certain health risks in comparison with a wooden pallet.

In the example shown in FIG. 3, a basic rearing unit BU comprises four columns of five stacked crates. Other configurations are possible, for example stacking more or fewer crates in columns, a single column of crates, or two columns of crates. The shape of the crates, in particular the general shape of their base, which is typically square or rectangular, can be adapted to the desired structure of the basic units.

For example, four stacks of crates with a rectangular base of approximately 60 cm long by 40 cm wide can completely cover a square pallet 120 cm wide. Six stacks of crates with a square base of approximately 40 cm side by side can be used to entirely cover such a pallet. It can also be decided to only place four stacks of crates with a 40 cm square base thereon, with or without spaces between them. Two stacks of crates with a rectangular base of approximately 80 cm by 60 cm can cover this one and the same pallet. Stacks of crates of different sizes can also be used, for example a stack of crates of approximately 80 cm by 60 cm and two stacks of crates of approximately 60 cm by 40 cm.

In order to cover a half-pallet 80 cm long by 60 cm, a stack of crates with a rectangular base approximately 80 cm by 60 cm, two stacks of crates of approximately 60 cm by 40 cm, or four stacks of crates approximately 40 cm by 30 cm can be used for example.

Numerous other combinations can be envisaged.

The height of a complete basic rearing unit can for example be comprised between 160 and 230 cm, and typically of the order of 200 cm making it possible to conform to conventional pallet racks which can comprise the first zone Z1. Thus, the number of stacked containers (in columns of containers) can be ten or more, potentially 15, or even more than 25.

A basic unit can comprise, in addition to a pallet and containers, a cover covering the upper containers (the last containers at the top of the stacks). This cover can have one or more functions including:
    closing the upper face of the upper containers;
    mechanical support of the stacks, being particularly necessary in order for the basic units to bear the horizontal accelerations undergone during the movements thereof;
    supporting a control sensor, such as a thermometer, a hygrometer, an oxygen sensor, a carbon dioxide sensor,
    supporting a lighting device, preferentially of the LED type, etc.

Different possible organizations of the first zone Z1 are shown, according to diagrammatic views, in FIGS. 4 and 5.

In FIG. 4, the first zone Z1 comprises two aisles, A1, A2 between racks R1, R2, R3 and R4, making it possible for two storage/retrieval machines T1, T2 respectively to move around. Each compartment in a rack represents a space for storing a pallet, or a column of storage spaces. The storage/retrieval machine T1, T2 can move in the aisle A1, A2 with which it is associated, and take a pallet in one of the spaces in the racks, so as to move it either to an interface with the second zone (not shown in FIG. 4), or to another space in the first zone Z1. In the example shown here, an air curtain 4 is arranged between certain pallet spaces. This air curtain 4 makes it possible to isolate various parts of the first zone Z1, respectively allocated to various growth stages of the insects (or larvae, or nymphs) requiring different environmental conditions. Whatever the general organization of the first zone Z1, several air curtains can be arranged in order to isolate several parts of said first zone Z1 from one another.

Partitioning the zone Z1 in several parts or silos makes it possible to reduce the risk of the spread of diseases. A silo can for example be constituted by two rows of racks equipped with a storage/retrieval machine in between the two rows.

This partitioning of silos can utilize air curtains, or any other partitioning means making it possible to separate two zones in order to be able to ensure therein two different atmospheric conditions (temperature, hygrometry, etc.) and sanitary separation between the silos. For example, physical partitions can be utilized. The first zone Z1 can comprise several different stores, separated by physical partitions. In this case, each store can be equipped with one or more automated devices for the movement of the basic units.

Typically, whatever the organization of the first zone Z1, it can be physically divided by air curtains or virtually divided into sub-zones dedicated to the different stages of maturity of the insects or to several rearing process conducted in a farm. For example three parallel processes can be identified, namely: a process called production process, which relates to the development of eggs or juveniles up to a larval stage of a given maturity that can correspond to the final product of the rearing before any transformation, a process called reproduction process, which relates to the development of eggs or juveniles up to the stage of young adults, and a process called egg-laying process, which relates to the production of eggs or juveniles by adult insects.

In FIG. 5, the first zone Z1 comprises racks R1, R2, R3 and R4 and storage/retrieval machines T1, T2, on either side of these racks R1, R2, R3, R4. Each rack is of the type allowing automated progression of the pallets. Typically, at a given stage of a rack R1, R2, R3, R4, a first storage/retrieval machine T1 can introduce a basic rearing unit into the rack in question. The basic unit then progresses in the rack via a motorised system or under the influence of gravity (for example on a roller system). The progression can take place following the removal by a second storage/retrieval machine T2 of a basic unit having progressed to one end of the rack opposite to the end of introduction by the first storage/retrieval machine. An air curtain 4 ensures separation between certain parts of the first zone Z1, in this case between two series of racks.

Whatever the variant of the invention in question, an air curtain of the order of 1 m to 2 m wide (over the entire height of the racks) and typically 1.6 m, is preferable for isolating the parts in question or silos of the first zone.

Figure 6:
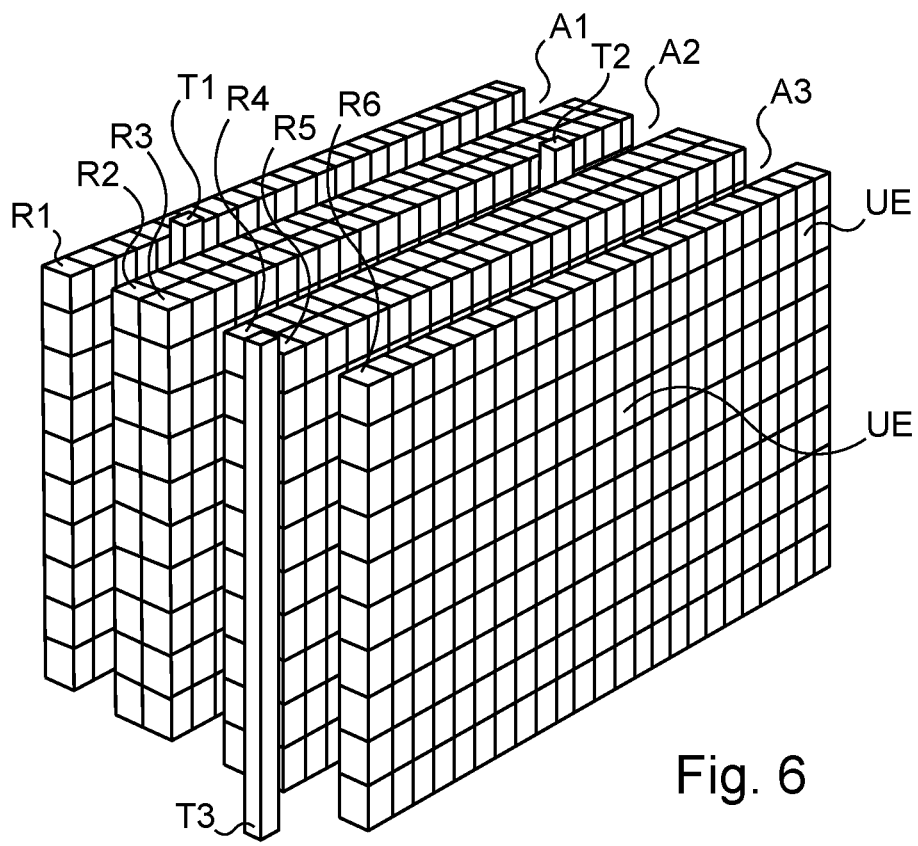

FIG. 6 shows, in a diagrammatic three-dimensional view, a possible arrangement of a first zone Z1 of a farm according to an embodiment of the invention. The organization shown corresponds to a variant of the organisation shown in FIG. 4, with three aisles A1, A2, A3 between the racks R1, R2, R3, R4, R5 and R6.

In this configuration with three aisles, three storage/retrieval machines T1, T2, T3 are used. However, storage/retrieval machines configured to each be able to serve several aisles can alternatively be used.

Moreover, according to this general principle of organization, it is possible to almost endlessly expand the first zone Z1 according to the floor space available by increasing the length of the racks and/or the number of racks, and according to the vertical space available by increasing the height of the racks, which makes it possible to considerably increase the productivity of the unit, in particular the spatial productivity thereof (i.e. the production by weight relative to the floor space used).

In the case that the racks are of a significant height, it can be necessary to ensure an air circulation that is sufficient to homogenize the temperature in a given zone (warm air tending to rise in the absence of a planned flow).

Figure 7:
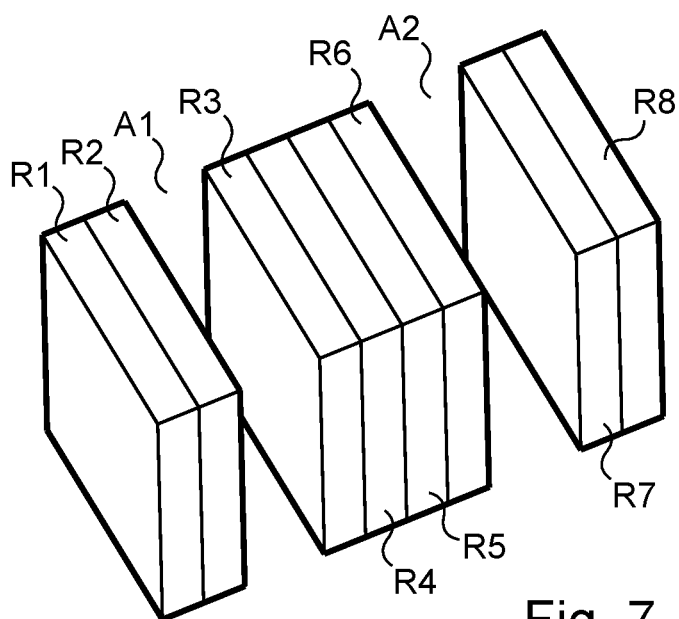
FIG. 7 shows, in a diagrammatic three-dimensional view, a variant of the first zone shown in FIG. 6.

FIG. 7 shows, in a diagrammatic three-dimensional view, another variant of the organization of a first zone Z1 according to an embodiment of the invention. According to this variant, the racks R1 to R8 are organized by groups of two, and each storage/retrieval machine capable of moving in the aisles A1, A2 is double depth, making it possible to collect a pallet or a palletized basic rearing unit on a rack in the second row if the corresponding space of the rack in the first row is empty. In other variants, the storage/retrieval machine can make it possible to collect pallets in a third row. Moreover, certain double or triple storage/retrieval machines make it possible to collect two or three pallets or basic units simultaneously.

Figure 8:
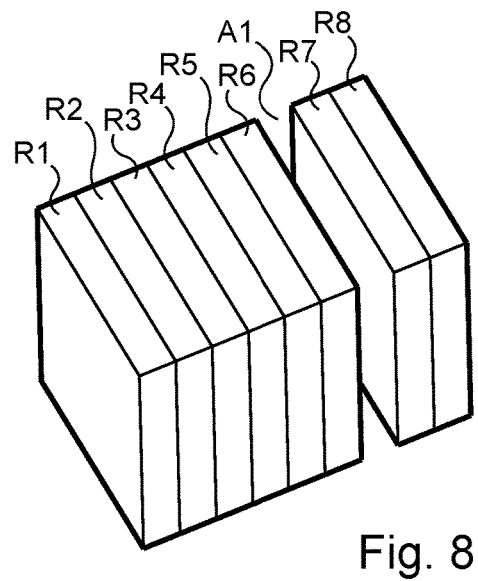
FIG. 8 shows an example of the organization of a first zone of a farm according to another embodiment of the invention.

FIG. 8 shows an example of the organization of a first zone of a farm according to another embodiment of the invention.

In the configuration shown, three to twenty racks are grouped together. In this instance, in the example shown, the racks R1 to R6 are grouped together. A storage/retrieval machine is configured to be able to run in the aisle A1. The aisle A1 separates the racks R1 to R6 from the racks R7 and R8. In this embodiment, the storage/retrieval machine provides a moving robot suitable for retrieving a basic unit in the desired row of the rack of the group of racks R1 to R6, if the rows between the aisle A1 and the desired row are empty. Numerous variants of this embodiment can be envisaged by adapting the number of adjacent rows of racks, or the number of aisles utilized.

Of course, the examples given in FIGS. 4 to 8 of the first zone Z1 can also correspond to the organization of a single silo of a first zone Z1 divided into as many physically partitioned stores as there are silos that make up the first zone Z1.

Figure 9:
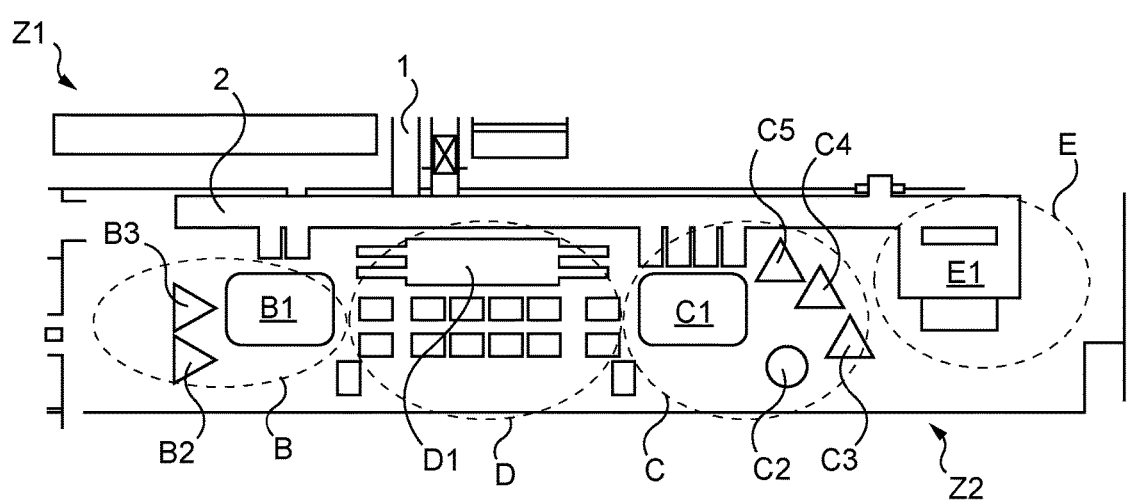
FIG. 9 shows, in a diagrammatic view, an example of the organization of a second zone of a farm according to an embodiment of the invention.

FIG. 9 shows, in a diagrammatic view, an example of the organization of a second zone Z2 of a farm according to an embodiment of the invention.

The example of a second zone Z2 shown in FIG. 9 is represented within the context of the example farm in FIG. 1. In particular, FIG. 9 shows the interface 1 with the first zone Z1. A conveyor system, namely in the example shown a belt conveyor 2, ensures the movement of the basic units or if applicable, the degrouped containers. A storage/retrieval machine, after selecting a pallet from the first zone Z1, places the latter on a zone of the belt conveyor 2 forming an interface 1 between the first zone Z1 and the second zone Z2, or any other device allowing the pallet to be sent to said belt conveyor 2 at the time desired. In the example shown here, the palletized basic units are directed by the belt conveyor 2 to the depalletization (and palletization) zones, in this case a first logistics zone B1 and a second logistics zone B2.

Generally, the example second zone Z2 shown here is organized in four sub-zones called islands, referenced respectively B, C, D and E. The islands B, C, D and E are associated with one or more rearing operations, for which they are more or less specialized.

In the example shown, the island E corresponds to a station for feeding the insects (or larvae, or nymphs). The feeding island E1 is equipped with a feeding device E.

According to different variants of the invention, the feeding either requires, or does not require, the containers forming the basic rearing units to be depalletized and degrouped. The depalletization can consist of separating each container of a basic unit from one another, in order to obtain a set of individual containers, or separating one basic unit into groups of containers (typically four to six containers).

The depalletization and the palletization, in the feeding island E as well as at the level of the first and second logistics zones B1, C1, can for example be carried out using a polyarticulated handling robot, for example a six-axis robot or a seven-axis robot. Such a robot can allow more generally handling of the rearing containers at speeds, accelerations, and maintaining a position, compatible with insect rearing.

The feeding device E1, whether or not the containers of the basic unit are, or are not, degrouped, must ensure a substantially uniform distribution of food in the containers.

The feeding island E can optionally allow water to be provided in the rearing containers. This provision of water can be carried out according to various alternative or additional modes: by periodically filling a dedicated tank of the containers, by fogging or pouring, by provision of water-rich food or material or water-enriched food or material.

Provision of a nutrient can also be carried out with the provision of water.

In the example shown, the island D is specialized in washing the rearing containers. It can in particular comprise one or more washing tunnels D1 suitable for washing the rearing compartments and/or pallets.

In the example shown here, the washing island D is configured in order to allow, when necessary, the supply of clean containers to islands B and C.

In the example shown, islands B and C correspond to a first modular island B and a second modular island C. The islands B and C are called modular in that they comprise a certain number of items of equipment that can be easily interchanged or upgraded so that they can easily be specialized for various rearing operations. In the configuration shown, the modular islands B, C each comprise a logistics zone B1, C1 equipped with a polyarticulated handling robot, for example a six-axis robot or a seven-axis robot. The robot with which these zones are equipped allows rearing containers to be degrouped when this is necessary for the subsequent carrying out of a rearing operation, and optionally the grouping together and palletization of the containers into basic units after carrying out a rearing operation at the level of the corresponding island.

The island is also configured in order to allow rearing operations to be implemented on basic units or containers. The island thus comprises one or more stations, or one or more machines, to which the basic units or containers must be sent. This function can be partially ensured by the handling robot, for example for placing a container on a conveyor bringing the basic unit or the container to a given station.

In the example shown, the first modular island B comprises a first air sifter B2, configured for separating live larvae, dead larvae and droppings. The first modular island B also comprises in particular a second air sifter B3, configured for the grading of the (live) larvae, i.e. the segregation of the larvae as a function of their size or their weight.

In the example shown, the second modular island C comprises a screen C2, configured for the separation between adult insects, eggs, and rearing substrate (medium added to the containers suitable for the life of the insects or larvae or nymphs). This can be in particular a series of sieves, the successive sieves separating the stages being increasingly fine in order to carry out the aforementioned separation. The second modular island C also comprises a third air sifter C3, configured for the separation between adult insects, larvae and nymphs. The second modular island C also comprises a fourth air sifter C4, configured for the separation between live adult insects and dead insects. The second modular island C also comprises a fifth air sifter C5, configured for the separation between larvae and nymphs.

The organization of the farm, and in particular of the second zone Z2, given here by way of example, allows the implementation of all of the periodic operations of insect rearing, from the egg up to obtaining adult insects having the desired level of growth. Many other modes of organization are possible, utilizing a larger or smaller number of islands or stations.

A farm according to the invention is also advantageously equipped with a device making it possible to monitor carrying out the different rearing operations during said rearing. In particular, the rearing process follows a succession of steps, i.e. typically a precise ordering of the rearing operations carried out following a predefined calendar, which can optionally be corrected during rearing, depending on the development of the insects' growth (or larvae or nymphs). In order to be able to monitor the progress of the rearing process efficiently, the farm is advantageously provided with a system for monitoring the basic units, and/or certain containers, and/or each of the containers.

The system for monitoring the basic units, and/or certain containers, and/or each of the containers can in particular utilize RFID (radio frequency identification often known as radio-identification) technology. An RFID tag can if appropriate be associated with the basic units, or containers, with reader systems allowing their identification being arranged in the farm, typically at the level of the interface between the first zone and the second zone (in order to manage the position of the basic unit in the racks of the first zone Z1), and at the entry to and/or the exit from the different stations at which the rearing operations are carried out. The RFID system implemented can also allow the instant identification of the set of compartments constituting a pallet. This RFID system is advantageously linked to a database that allows the traceability of each of the containers to be guaranteed. The traceability relates to the entire rearing process, from the raw materials used for rearing, to the insects (feed, substrate, etc.) up to killing and the transformation into finished products.

Other means for identification and collection of corresponding data can be used successfully, for example wireless communication, in particular according to a WiFi, Bluetooth or Zigbee (registered trade marks) protocol. A low-throughput system utilizing low-frequency radio waves can also be successfully implemented.

The farm is also advantageously equipped with a computerized system for monitoring production, associated with monitoring means of the RFID type or another type. The production can thus be driven in an automated manner, the system being able typically to associate certain operations with certain basic rearing units, and in due time to control the collection of a given basic rearing unit in the first storage zone, carry out the desired sequence, and the return of the basic unit to a given position.

Typically, the stage of development and growth of the insects (eggs, larvae, nymphs, adult insects) in one and the same basic rearing unit is theoretically identical. To this end, the insects in one and the same basic unit are advantageously 'synchronized', i.e. originating from eggs laid at a maximum interval of a few days, then sorted from the larval stage by size or by maturity. The monitoring of the basic units is thus generally sufficient for controlling the automated devices of the farm, for example storage/retrieval machines can be used to recover a unit in the first zone Z1 of the farm and take it to the second zone Z2 in order to carry out a given operation, then devices making it possible to direct the basic unit in the second zone Z2 to the desired station or stations.

Monitoring of certain particular containers can allow for example the periodic withdrawal and sampling of these particular containers to carry out checks for implementation of controls or assessments.

Finally, individual monitoring of the containers, requiring the identification of each of said containers, allows full and individualized monitoring of the rearing process. It makes it possible in particular to reconstitute basic units when required during the rearing with containers originating from other basic units or with new containers.

A rearing farm according to the invention can be used for rearing many species of insects, by means of minor adaptations, typically in the technical definition of the rearing containers, and in the calibration of the machines used for feeding and for sorting operations. Generally, a single species is reared in one farm. Several species can also be reared, preferably in separate parts of the farm. Within the context of a farm suitable for simultaneously rearing several species of insects, certain synergies can be exploited. Typically, certain larvae, live or dead insects of one species, or the by-products of production and rearing, can be used to feed another species.

The product(s) of interest ultimately obtained, after reusing the rearing products, are obtained from insects. As mentioned previously, by "insects" is meant insects regardless of the stage of development, such as an adult or larval stage or a nymph stage. Preferably, the insects utilized in the process according to the invention are edible.

More particularly, the insects can be selected from the group constituted by Coleoptera, Diptera, Lepidoptera, Isoptera, Orthoptera, Hymenoptera, Dictyoptera, Hemiptera, Heteroptera, Ephemeroptera and Mecoptera, preferably, from Coleoptera, Diptera, Orthoptera and Lepidoptera.

Preferentially, the insects are selected from the group constituted by *Tenebrio molitor* (or yellow mealworms), *Hermetia illucens*, *Rhynchophorus ferrugineus*, *Galleria mellonella*, *Alphitobius diaperinus*, *Zophobas morio*, *Blattera fusca*, *Musca domestica*, *Chrysomya megacephala*, *Locusta migratoria*, *Schistocerca gregaria*, *Acheta domesticus* and *Samia ricini*.

Favourable conditions, in particular in the first zone where the insects are stored during their growth, can allow rapid development and reproduction of the insects. For example, the full developmental cycle of the yellow mealworm, from the egg to the full grown adult, can take from two to three months at a temperature of 15° C. to 35° C., while it can take a year in the natural environment.

A farm according to the invention thus allows large-scale insect rearing with minimal costs by virtue of its high automation and the optimization of the devices and processes utilized. For example, a storage/retrieval machine can typically perform up to five hundred movement operations per hour. Moreover, it makes it possible to move the pallets that can be organized in order to each carry a large quantity of insects. Therefore, such a device makes it possible to organize a very high flow rate while having a very high volume density of insects within the farm.

Moreover, the rearing operations are carried out in a zone of limited size at stations which are specialized and thus optimized for these operations. The growth of the insects takes place in a zone with a controlled, or even driven, atmosphere (temperature, hygrometry, etc.), in order to propose optimal growth conditions for the insects at all stages from the egg to the adult.

The control device can thus allow the driving or regulation of controlled environmental parameters, or of parameters associated with these.

The zone for storing insects can also be particularly optimized in terms of space, by utilizing storage in racks that can have a significant height, which reduces the floor space required. By way of example, it is estimated that by using racks 12 metres in height in the first zone Z1, a farm according to the invention could allow the production of more than 8,000 tonnes annually of proteins (as dry material) per hectare in use, while a soya crop allows the production thereof of one to five tonnes per hectare annually, and rearing pigs or chickens in batteries allows the production of an equivalent of a few tens of tonnes per hectare annually.

The farm proposed in the invention in particular makes it possible to utilize a rearing method based on a sequential ordering in two separate zones of single operations alternating with "passive" periods of storage for the growth of the insects. Such a method is suitable for the production of insects on an industrial scale. By way of example, a farm of a modest size according to the invention could produce a minimum of one tonne of larvae daily, having a zone suitable for the storage of fifty tonnes of insects (eggs, larvae, nymphs and adults) distributed over 500 pallets. The rearing operations in this case require the movement of approximately 140 pallets daily. By virtue of the organization proposed in the invention, these values can be increased and improved almost without limit. A large-scale industrial operation, responding to the needs of the markets in animal feedstuffs for example, could thus typically lead to the adoption of values fifty to one hundred times greater than those mentioned previously, depending on the markets envisaged.

Finally, rearing in a farm according to the invention can be carried out with means and processes allowing rigorous control and monitoring, limiting the health risks in the farm.

The invention claimed is:

1. A farm for rearing insects, comprising a first zone (Z1) in which the insects being reared are stored in containers (31, 32) while they grow and a second zone (Z2) comprising at least one station configured in order to carry out a rearing operation on the insects of a container or on said container;
   characterized in that the containers (31, 32) are grouped together in the first zone (Z1) into sets of palletized containers (31, 32) called basic units (BU), the first zone (Z1) comprising pallet racks (R1 . . . R8) in which the basic units (BU) can be arranged;
   the first zone (Z1) also being equipped with an automated device configured in order to move the basic units (BU) between the first zone (Z1) and an interface (1) with the second zone (Z2).

2. The farm for rearing insects according to claim 1, in which the automated device comprises a storage/retrieval machine (T1, T2, T3) capable of moving along or between the racks (R1 . . . R8).

3. The farm for rearing insects according to claim 1, in which the automated device is suitable for moving inside the racks.

4. The farm for rearing insects according to claim 1, in which the containers (31, 32) are stackable crates, basic units (BU) comprising a plurality of crates stacked in one or more columns on the pallet (33).

5. The farm for rearing insects according to claim 4, in which a basic unit (BU) comprises one to four columns each constituted by four to twenty-five crates.

6. The farm for rearing insects according to claim 4, in which a basic unit (BU) comprises one to four columns each constituted by four to thirty-five crates.

7. The farm for rearing insects according to claim 1, in which the basic units comprise a rack suitable for receiving the containers so as to form one or more columns of containers.

8. The farm for rearing insects according to claim 1, in which the basic units (BU) have a height comprised between 1.80 m and 2.40 m, and preferably between 2 m and 2.20 m.

9. The farm for rearing insects according to claim 1, in which the basic units (BU) have a height comprised between 1.80 m and 3 m, and preferably between 2 m and 2.80 m.

10. The farm for rearing insects according to claim 1, in which the racks (R1 . . . R8) are configured in order to store from two to fifteen basic units (BU) heightwise, and one or two basic units (BU) depthwise.

11. The farm for rearing insects according to claim 1, in which the racks (R1 . . . R8) are configured in order to store from two to twenty basic units (BU) heightwise, and one to twenty-two basic units (BU) depthwise.

12. The farm for rearing insects according to claim 11, comprising a device for controlling at least one environmental parameter among the temperature, the hygrometry of the air, the atmospheric pressure, the light and its frequency, the oxygen content of the air, the volatile organic compound content of the air and the fine particulate matter content of the air, configured in order to apply a different environmental parameter value to each set of racks.

13. The farm for rearing insects according to claim 1, in which the first zone (Z1) is divided into silos, intended to store larvae or insects at different stages of growth and/or of different species, said silos being separated by partitioning means.

14. The farm according to claim 1, in which the second zone can comprise an automated conveyor system for moving the basic units (BU) or of containers (31, 32) removed from the group to the at least one station of said second zone (Z2).

15. The farm according to claim 1, in which the second zone (Z2) comprises a station for depalletizing and degrouping the containers (31, 32).

16. The farm according to claim 1, in which the second zone (Z2) comprises a station for grouping together the containers (31, 32) into basic units.

17. The farm according to claim 1, in which the second zone (Z2) comprises a plurality of stations, each station being configured for one or several rearing operations selected from:
    feeding;
    providing water;
    grading the insects by size, weight, volume or density;
    sorting live and dead larvae and droppings;
    sorting live adults and dead adults;
    sorting live nymphs and dead nymphs;
    sorting at least two stages of development of the insects between eggs, larvae, nymphs and adults,
    separating insects and the substrate that has not been consumed;
    sorting insects and eggs;
    adding insects to a rearing container;
    killing or destroying the insects;
    identifying insects having symptoms of disease;
    washing the containers (31, 32).

18. The farm according to claim 17, in which a station comprises a viewing and/or sampling tool configured in order to analyze the physiological state of the insects, larvae, nymphs.

19. The farm according to claim 17, comprising a station configured for grading the adult insects by size, weight, volume or density and/or sorting the live and dead larvae and the droppings and/or sorting adult insects, larvae or nymphs, containing a separation device according to the density and the air intake.

20. The farm according to claim 17, comprising a station configured for grading the live larvae by weight or by volume and/or sorting the live and dead larvae, live and dead adult insects, live and dead nymphs, eggs, substrate and droppings, and/or sorting insects according to the stage of development, comprising an optical sorting device.

21. The farm according to claim 17, comprising a station configured for grading live larvae and/or sorting live and dead larvae, live and dead adult insects, live and dead nymphs, eggs, substrate and droppings, comprising a screen, a vibrating table or a densimetric table.

22. The farm according to claim 17, comprising a station configured for grading live larvae and/or sorting live and dead larvae, live and dead adult insects, live and dead nymphs, eggs, substrate and droppings, comprising a roller grader.

23. The farm according to claim 1, comprising a device for identifying containers or basic units (BU) suitable for being utilized by electronic means.

24. The farm according to claim 1, also comprising a set of sensors comprising:
    a weight sensor configured in order to determine the weight of a basic unit or of a container; and/or
    a colour sensor, configured in order to determine the colour of the insects, nymphs or eggs, substrate, water and/or droppings in a container; and/or
    a thickness or volume sensor configured in order to determine the thickness or the volume of substrate in a container;
    a size sensor, configured in order to determine the size of the insects, nymphs or eggs in a container.

* * * * *